(12) United States Patent
Kleinszig et al.

(10) Patent No.: US 9,592,025 B2
(45) Date of Patent: Mar. 14, 2017

(54) METHOD, APPARATUS AND X-RAY RECORDING SYSTEM FOR VISUALIZATION OF AN X-RAY REGION

(71) Applicant: SIEMENS AKTIENGESELLSCHAFT, Munich (DE)

(72) Inventors: Gerhard Kleinszig, Forchheim (DE); Wei Wei, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 14/715,808

(22) Filed: May 19, 2015

(65) Prior Publication Data
US 2015/0327824 A1 Nov. 19, 2015

(30) Foreign Application Priority Data

May 19, 2014 (DE) .................. 10 2014 209 456
Mar. 20, 2015 (DE) .................. 10 2015 205 096

(51) Int. Cl.
| A61B 6/08 | (2006.01) |
| A61B 6/00 | (2006.01) |
| G09G 3/20 | (2006.01) |
| G06T 5/50 | (2006.01) |
| G06T 7/00 | (2006.01) |
| G06T 19/00 | (2011.01) |

(52) U.S. Cl.
CPC .............. *A61B 6/582* (2013.01); *A61B 6/08* (2013.01); *A61B 6/461* (2013.01); *G06T 5/50* (2013.01); *G06T 7/0038* (2013.01); *G06T 7/0081* (2013.01); *G06T 19/006* (2013.01); *G09G 3/2003* (2013.01); *A61B 6/4441* (2013.01); *A61B 6/508* (2013.01); *A61B 6/589* (2013.01); *G06T 2207/10016* (2013.01); *G06T 2207/10116* (2013.01); *G06T 2207/30004* (2013.01); *G06T 2207/30196* (2013.01); *G06T 2210/41* (2013.01); *G06T 2219/028* (2013.01); *G06T 2219/2004* (2013.01)

(58) Field of Classification Search
CPC .......... A61B 6/582; A61B 6/08; A61B 6/461; A61B 6/589; A61B 6/508; A61B 6/4441; G06T 5/50; G06T 7/0081; G06T 7/0038; G06T 19/006; G06T 2207/10016; G06T 2219/2004; G06T 2210/41; G09G 3/2003
USPC .................................................... 378/206
See application file for complete search history.

(56) References Cited

U.S. PATENT DOCUMENTS

2011/0249793 A1* 10/2011 Lalena ............... A61B 6/46
378/62
2013/0077745 A1* 3/2013 Wang ............... A61B 6/52
378/62

* cited by examiner

*Primary Examiner* — Michael Maskell
(74) *Attorney, Agent, or Firm* — Laurence Greenberg; Werner Stemer; Ralph Locher

(57) ABSTRACT

A visualization of an X-ray region during the production of an X-ray recording of an object is produced. In order to reduce radiation exposure for a physician and/or the patient during X-ray recordings, a proposal is made to record a video image of a region, which is captured by a beam from the X-ray source, of the object, to display the video image and to represent at least a portion of the beam in the displayed video image.

9 Claims, 3 Drawing Sheets

METHOD, APPARATUS AND X-RAY RECORDING SYSTEM FOR VISUALIZATION OF AN X-RAY REGION

CROSS-REFERENCE TO RELATED APPLICATION

This application claims the priority, under 35 U.S.C. §119, of German applications DE 10 2014 209 456.9, filed May 19, 2014, and DE 10 2015 205 096.3, filed Mar. 20, 2015; the prior applications are herewith incorporated by reference in their entireties.

BACKGROUND OF THE INVENTION

Field of the Invention

The invention relates to a method, an apparatus and a computer program for visualizing an X-ray region while producing an X-ray recording of an object. Moreover, the invention relates to an X-ray recording system having such an apparatus.

Frequently, when producing X-ray recordings, radiation exposure for the treating physician through primary radiation emitted by an X-ray source becomes a problem. The radiation exposure for the physician can here be considerable, in particular in trauma surgery.

A further problem when producing X-ray recordings is the correct positioning of the patient relative to the X-ray source. Incorrect positioning can lead to unnecessary radiation exposure of the patient, for example because X-ray recordings must be repeated. Hitherto, usually only laser crosshairs aimed at the patient have been used to approximate the position of the patient relative to the beam of the X-rays.

The object, of which an X-ray recording is intended to be produced, does not necessarily have to be a person, i.e. a patient. The object may also be an animal or another, dead object. To the extent that the respective text context does not state anything to the contrary, the terms "object" and "patient" are therefore used synonymously below.

SUMMARY OF THE INVENTION

It is one object of the invention to reduce the radiation exposure for the physician and/or the patient during X-ray recordings.

With the foregoing and other objects in view there is provided, in accordance with the invention, a method for visualizing an X-ray region formed during a production of an X-ray recording. The X-ray recording relates to at least one region of an object located in an object plane, the at least one region is disposed between an X-ray source and an X-ray receiver and is captured by a beam from the X-ray source. The method include recording a video image of the region of the object, displaying the video image, and representing at least a portion of the beam in the video image displayed.

The invention proposes to record an image of at least one region of an object that is captured by a beam from the X-ray source, to display the image and to represent at least a portion of the beam as an X-ray region in the displayed image. As a result, the physician can position the patient correctly, and typically more precisely than has been possible to date. The physician also receives information on the position of the high-radiation region and can thus reduce his own radiation exposure. In other words, the visualization of the X-ray region fulfils a double function. Not only can it serve to represent a hazard region that is subject to the X-rays, but can also serve for more accurate positioning of the patient in the X-ray region.

The recorded image, in which the high-radiation region is represented, is a video image. In other words, not just a single patient image is taken. Instead, a video is recorded of the patient or of the object to be examined. This makes possible not only a representation of a specific recording region at a specific time, but also a common representation of a real-time recording of the patient and of a hazard region, both before and also during the emission of the X-rays.

A core concept of the invention is the visualization of the region of the object environment that is exposed to the X-rays. Preferably, to this end, the entire volume of the beam emitted by the X-ray source is displayed in the recorded image. The image is then preferably a three-dimensional, perspective display of the region of the object that is captured by the beam from the X-ray source. The beam is then likewise displayed in three-dimensional manner and preferably set off in terms of color and/or structure such that it is distinct and sufficiently different from the remaining image information, in particular the object.

A visualization of the entire beam is, however, comparatively difficult to realize. In one embodiment of the invention, a proposal is therefore made to represent not the entire beam but only a portion of the beam. This portion of the beam can be a two-dimensional or a three-dimensional portion of the beam. Preferably, a virtual recording region of the X-ray recording is represented as a portion of the beam. According to the invention, an intersecting area between the beam and an object that is disposed in the beam or captured by the beam is displayed. In other words, the actual recording region of the X-ray recording is visualized as a high-radiation region by way of a virtual recording region.

In one embodiment of the invention, this virtual recording region is associated with the patient as the object to be examined. In other words, the virtual recording region corresponds to the actual desired recording region of the X-ray recording. The intersecting area between the beam and the object plane is used as the virtual recording region. The object plane is in this case the operating table, the patient couch or the like. In other words, the representation of the virtual recording region takes place in the patient plane. That means that the virtual recording region displays the actual size of the recording. It is then possible using the display of this virtual recording region to set an optimum positioning of the patient relative to the X-ray, as a result of which the conventional laser crosshairs, which only mark the center of the recording region, can be replaced. In addition to this setting of the position and/or location of the patient, it is likewise possible using the display of the virtual recording region to position the patient with respect to the desired size of the recording region.

Owing to the conical shape of the beam, the actual high-radiation region can be located above the patient, that is to say where the physician's hands will be located, but can be larger than a virtual recording region which corresponds to a recording region that is located in the patient plane. In a further embodiment of the invention, for the protection of the physician, provision is therefore made for a virtual recording region which is larger than the actual recording region in the patient plane that relates to the patient to be calculated and displayed. In other words, the invention can also be used such that the represented virtual recording region relates not only to the patient but also to the hands of the surgeon or another object located within the volume of the beam. Therefore, the actual high-radiation region for this object is visualized independently of the location of the patient. If the virtual recording region is not displayed in the patient plane, but in that plane in which a further object is located, for example a physician's hand, it is therefore possible to ensure that the physician can obtain knowledge of the position of the beam and thus of the high-radiation region in a simple manner and thus always moves his hands outside the hazardous region.

In both cases of the calculation of the virtual recording region, that is to say both if the basis is the patient plane and also if the basis is an object plane that is different therefrom, it is possible with the representation of a virtual recording region according to the invention to ensure that objects which are not intended to be imaged, for example a metallic object which can contribute to the production of stray radiation, to artifacts in the 3D reconstruction and to an increase of the X-ray exposure by automated dose regulation, are not located within the beam. Instead, these objects can be removed from the recording region before the X-ray recording starts. As a result, the proportion of stray radiation as a further source of unnecessary radiation exposure can also be reduced.

For simple implementation of the invention, it is advantageous, independently of the type of the calculation of the virtual recording region, that an exact position determination of the object is not necessary. In the simplest case, the determination of the distance of the object from the X-ray source or from the X-ray detector suffices for displaying the virtual recording region or another suitable portion of the beam in the recorded image such that the displayed volume or the displayed area corresponds to a high-radiation region in the object environment.

One important advantage of the invention can also be found in that the actual recording region, which to date has often been estimated incorrectly, can be determined more accurately. This contributes to a reduction of the radiation exposure for the patient and the physician. In the best case, it is possible with a later recording region of the X-ray recording, which is set correctly from the beginning and is visualized in advance with the aid of the invention, to prevent unnecessary recording attempts and thus multiple recordings. This reduces not only the radiation exposure but it also shortens the operating time, as a result of which the risk of complications decreases. A significant advantage of the invention is that the representation of the high-radiation region, in particular of the virtual recording region, is already possible before the X-ray recording is produced, which is important in particular for the positioning of the object. In other words, with the aid of the visualization of the recording region, the physician can optimize the patient's location for the X-ray recording, before the actual X-ray recording including the emission of X-rays takes place. The physician detects the future high-radiation region even before the object is irradiated with X-rays, since this region is represented in the image. He can therefore remove his hands from the high-radiation region, for example, before the X-rays are triggered. Subsequently, that is to say after the X-rays are triggered, the display of the high-radiation region taking place during the X-ray recording serves for visual monitoring by the physician that no undesired objects are located in this region or enter this region, in particular not the physician's hands.

According to the present invention, it is therefore not only possible to display at least a portion of the beam, in particular in the form of a calculated virtual recording region, in the displayed image during the production of the X-ray recording, or more precisely during the emission of the X-rays. It is likewise possible to effect this display even before the X-rays are emitted.

The invention can be used in particular in two-dimensional X-ray recordings, but the representation of a virtual recording region can also be used for positioning the patient in the case of 3D X-ray recordings.

With particular advantage, the invention can be applied in mobile and stationary C-arm X-ray machines, since here the geometry, in particular the tube/detector distance, is known and remains constant, and the central X-ray is always perpendicular to the detector plane. The invention, however, can also be applied in other X-ray machines, in particular in conventional X-ray machines, although there the calibration of the camera system is more difficult to realize.

The use of the invention is independent of the type and the purpose of the X-ray recording. However, with particular advantage, the invention can be used in the field of trauma surgery, for example when reducing bone fragments.

With the foregoing and other objects in view there is provided, in accordance with the invention, an X-ray recording system. The X-ray recording system contains an X-ray source and an X-ray receiver for producing an X-ray recording of at least one region of an object located in an object plane. The at least one region is disposed between the X-ray source and the X-ray receiver and is captured by a beam from the X-ray source. The X-ray recording system further has an apparatus for visualizing an X-ray region for use in the X-ray recording system. The apparatus contains a video camera for recording a video image of the at least one region of the object, a screen for displaying the video image, and a device for representing at least a portion of the beam in the video image displayed.

Other features which are considered as characteristic for the invention are set forth in the appended claims.

Although the invention is illustrated and described herein as embodied in a visualization of an X-ray region, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
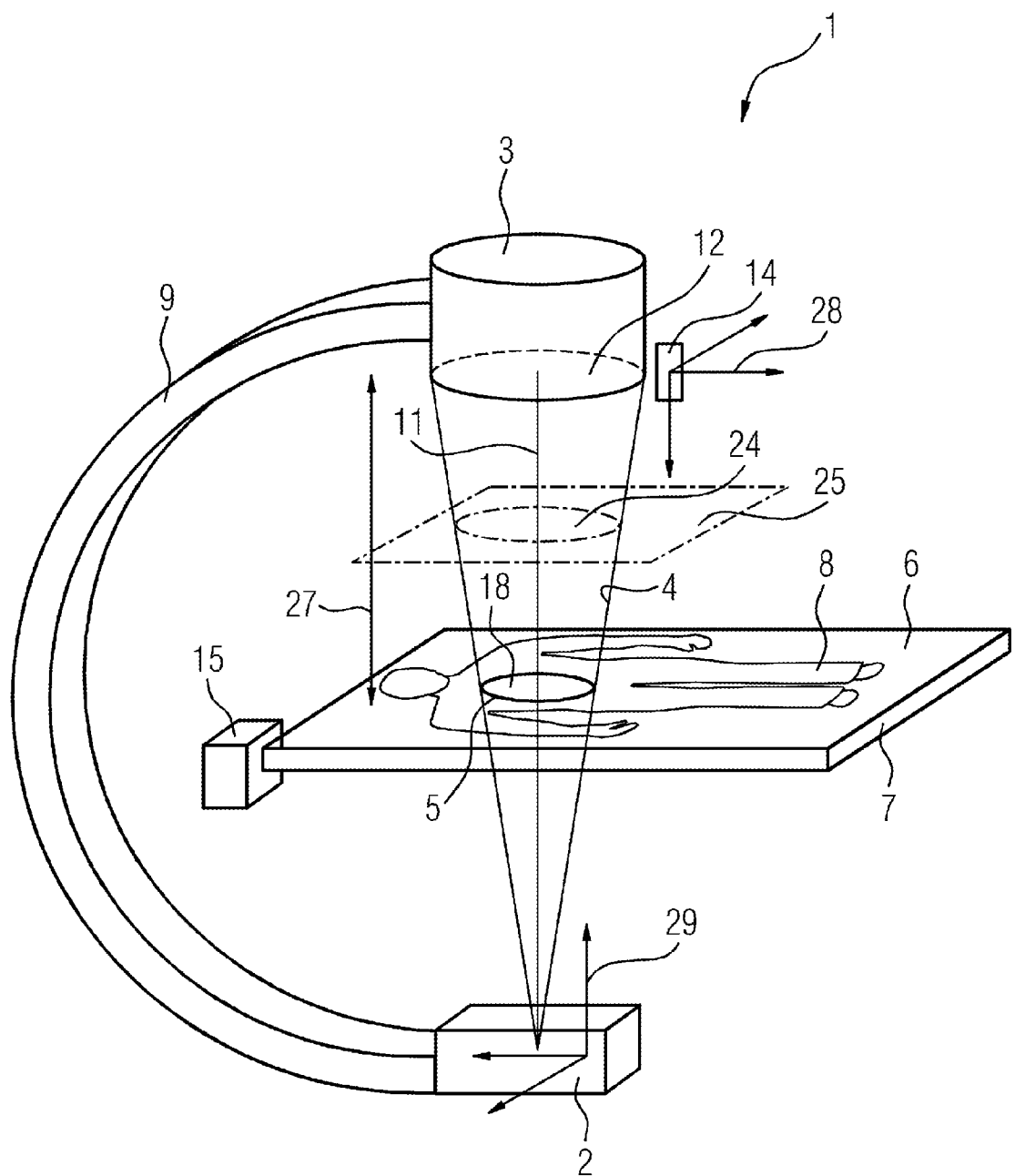
FIG. 1 is a diagrammatic, perspective view showing an X-ray recording system.

All the figures illustrate the invention only schematically and with its essential constituent parts. Identical reference numerals correspond here to elements of identical or comparable function.

Referring now to the figures of the drawings in detail and first, particularly to FIG. 1 thereof, there is shown an X-ray recording system 1 which contains an X-ray source 2 and an X-ray receiver 3 for producing an X-ray recording of at least one region 5 of a patient 8 located in a patient plane 6 on an operating table 7, which region is arranged between the X-ray source 2 and the X-ray receiver 3 and is captured by a beam 4 from the X-ray source 2. The X-ray recording here does not have to be limited to a portion of the patient 8; instead, it can involve the entire patient 8. The X-ray recording system 1 is a C-arm X-ray machine, the C-arm 9 of which can be adjusted in a known manner along its circumference in a specific angular range by way of a motor so as to obtain 2D projections from different projection angles. For the sake of simplicity, a point-shaped X-ray source 2 and a conical beam 4 are assumed. The X-ray receiver 3 is a flat-panel detector. The patient plane 6 is disposed parallel to the X-ray receiver 3. A central X-ray 11 is here perpendicular to a detector plane 12.

The X-ray recording system 1 furthermore contains an apparatus 13 for automatically visualizing an X-ray region. The apparatus 13 has a camera 14, a screen 15 and a representation device 16, see FIG. 3.

The camera 14 is configured for automatically recording an image 17 of the region 5 of the patient 8 that is captured by the beam 4 from the X-ray source 2. The image 17 preferably contains the entire region 5 and moreover also the environment of the region 5. However, the image 17 can also comprise only a portion of the region 5. The camera 14 is a video camera, and the recorded image 17 is a video image. The image 17 is already recorded before the X-ray recording procedure begins, that is to say before the X-ray source 2 emits a beam 4. Recording continues for the entire X-ray recording procedure. The camera 14 is advantageously disposed directly above the patient 8, such that it can produce recordings of the patient 8 and of the environment of the patient 8, in particular recordings of the space located above the patient 8 which corresponds to the viewing angle of the physician who typically likewise observes the patient 8 from above. The camera 14 is preferably arranged on the X-ray receiver 3. The camera 14 can be subsequently mounted on pre-existing X-ray receivers 3. Advantageously, however, the camera is integrated in the X-ray receiver 3.

The screen 15 is configured for the automatic display of the image 17 or a portion thereof. A screen 15 is understood to mean any display apparatus that is suitable for the purpose described here. A screen that is already present in the X-ray recording system 1 or an additional screen 15, which is used only to implement the invention, can be used as the screen 15.

The recorded image 17 is displayed substantially without delay, that is to say simultaneously with the recordings of the image 17 such that the patient 8 and the patient environment are displayed in real time on the screen 15.

The representation device 16 is configured for automatically representing a virtual recording region 18, corresponding to the intersecting area between the beam 4 and the patient plane 6, of the X-ray recording in the displayed image 17 on the screen 15. In the simplest case, a two-dimensional display of the virtual recording region 18 on the screen 15 is produced. Advantageously, the virtual recording region 18 is represented such that it overlays the likewise represented image 17 of the patient 8, such that the arrangement of the X-ray region relative to the patient 8 becomes clear at one glance. The virtual recording region 18 is here preferably represented as translucent, such that the physician can still recognize regions 19 of the patient 8 that are located thereunder.

In this context, it is advantageous if the representation device 16 is moreover configured such that the virtual recording region 18 can be optionally superposed on or removed from the displayed image 17.

The representation device 16 is configured for colored representation of the virtual recording region 18. In particular, the virtual recording region 18 is here represented in multiple colors. It is advantageous for quickly recognizing the hazard potential if the color representation occurs in dependence on the radiation exposure. The virtual recording region 18 illustrated in FIG. 2 has an inner core region 21, which is represented in red and indicates particularly high radiation exposure, and a rim region 22, which is represented in green and represents lesser radiation exposure.

The virtual recording region 18 is represented even before the X-ray recording is produced. Therefore, the patient 8 can be positioned correctly for the subsequent X-ray recording. This positioning also involves the setting of the size of the desired actual recording region 5, to the extent that the virtual recording region 18 is calculated such that it corresponds to the actual recording region 5.

If an additional screen 15 is used to display the image 17 and the virtual recording region 18, the screen is disposed preferably in the direct vicinity of the physician, that is to say either directly at the operating table 7, as in the example illustrated in FIG. 1, or at the X-ray receiver 3, such that the physician can gather information about the position of the patient 8 relative to the beam 4 without extraneous effort, with a quick look at the screen 15. The physician thus directly obtains details relating to the position of the actual recording region 5, and also about the position of his hands 23 and possibly other objects, such as for example medical instruments, within the beam 4.

The virtual recording region 18 which is represented on the screen 15 in the displayed image 17 becomes larger owing to the conical shape of the beam 4 the closer it gets to the X-ray receiver 3. The representation of a larger virtual recording region 24 makes sense if the physician's hands 23 that are positioned above the patient 8 would otherwise lie outside the typically displayed virtual recording region 18, even though they are located in the actual high-radiation region, that is to say within the cone of the beam 4. A larger virtual recording region 24, which corresponds to the actual high-radiation region above the patient plane 6, is represented with a dotted line in FIGS. 1 and 2. A virtual plane above the patient plane 6 here serves as the object plane 25. This larger virtual recording region 24 is displayed alternatively to and/or in chronological sequence with a first virtual recording region 18. In a particularly advantageous embodiment of the invention, a virtual recording region 18, which corresponds to the actual recording region 5 of the later X-ray recording, that is to say the intersecting area between the beam 4 and the patient plane 6, is represented before the X-ray recording begins, and a larger virtual recording region 24, which corresponds to the actual high-radiation region in a virtual object plane 25 above the patient plane 6, is represented for safety purposes thereafter, i.e. during the X-ray recording.

In the simplest case, the virtual recording region 18 is displayed on the screen 15 in the form of a round circular area if the camera 14 is aimed perpendicularly onto the X-ray receiver 3, that is to say if the angle of the camera recording corresponds to the direction of the central X-ray 11.

The size of the represented virtual recording region 18, that is to say in particular the diameter of the circular area, is dependent on the distance of the patient 8 from the X-ray receiver 3, or in other words, on the distance 27 of the patient plane 6 from the detector plane 12. If a larger virtual recording region 24 is intended to be represented, its size is calculated by the representation device 16 starting from the virtual recording region 18.

Figure 3:
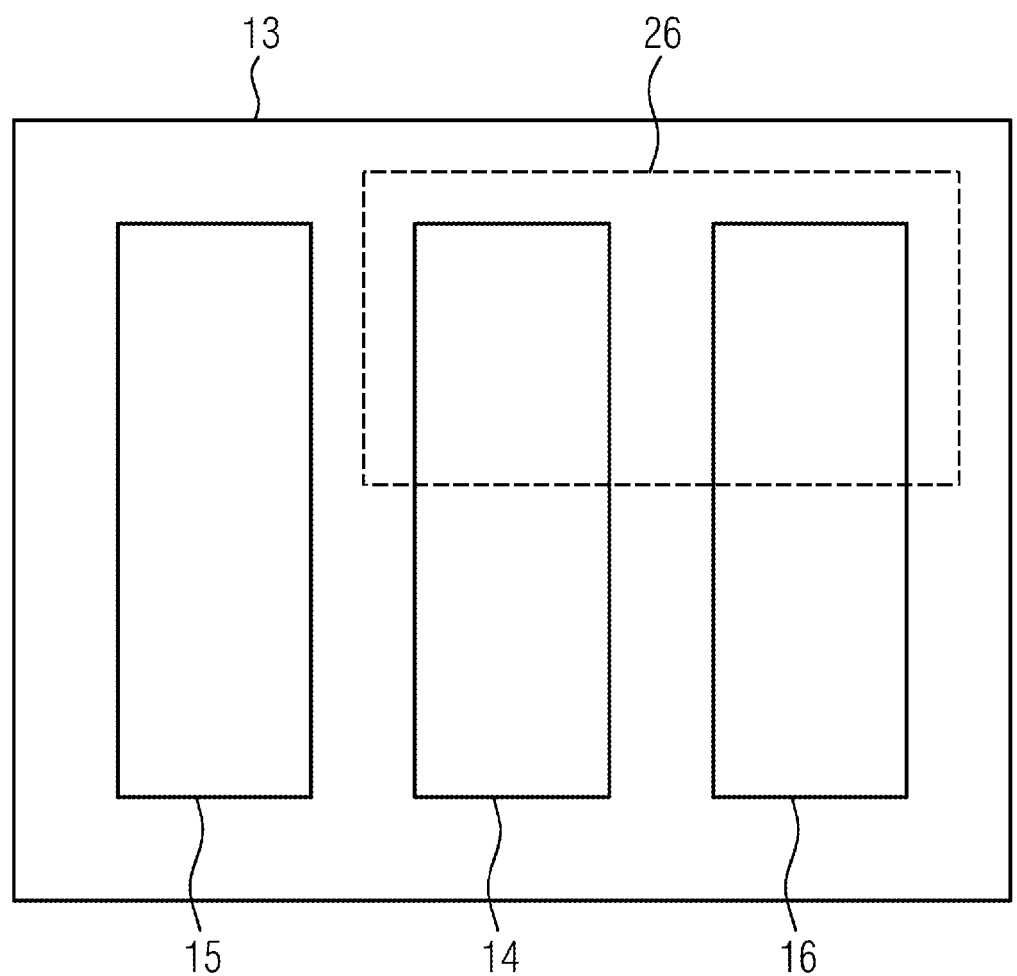
FIG. 3 is an illustration showing an apparatus according to the invention.

In correspondence with this dependency on distance, the representation device 16 furthermore contains a device 26, see FIG. 3, for automatically ascertaining the distance of the patient 8 from the X-ray receiver 3. Alternatively, the device 26 is configured for automatically ascertaining the distance of the patient 8 from the X-ray source 2.

In one embodiment of the invention, the distance 27 of the patient plane 6 from the detector plane 12 is ascertained with a camera 14 and suitable camera software. The camera software is configured for controlling, by way of a motor, the camera position and/or for controlling the camera function and/or for evaluating images produced with the camera 14. In a simple embodiment, the camera 14 is used to carry out a search for the laser crosshairs (not illustrated) that are projected onto the patient 8 and to calculate the distance of the patient plane 6 from the detector plane 12 on the basis of the marking. To this end, suitable calibration of the camera 14 or of the device 26 with respect to the X-ray recording system 1 is necessary. Here, different methods for calibrating are possible. By way of example, the calibration procedure contains a first calibration step for calibrating the two laser planes of the laser crosshairs with the camera system using a calibration plate (not illustrated) which is placed between the X-ray source 2 and the X-ray receiver 3, and is aimed by way of the laser crosshairs and moved parallel to the central X-ray 11 for a number of calibration recordings, and a subsequent, second calibration step for calibrating the camera system with the X-ray recording system. Hereby, the location of the central X-ray 11 in the coordinate system 28 of the camera 14 can be determined. After the calibration, the coordinate system 28 of the camera 14 is matched to the coordinate system 29 of the X-ray recording system 1, and transforms between the two coordinate systems 28, 29 are easily possible. Other methods for determining the distance are possible, for example it is possible to measure the distance by acoustic or classical optical means.

Figure 2:
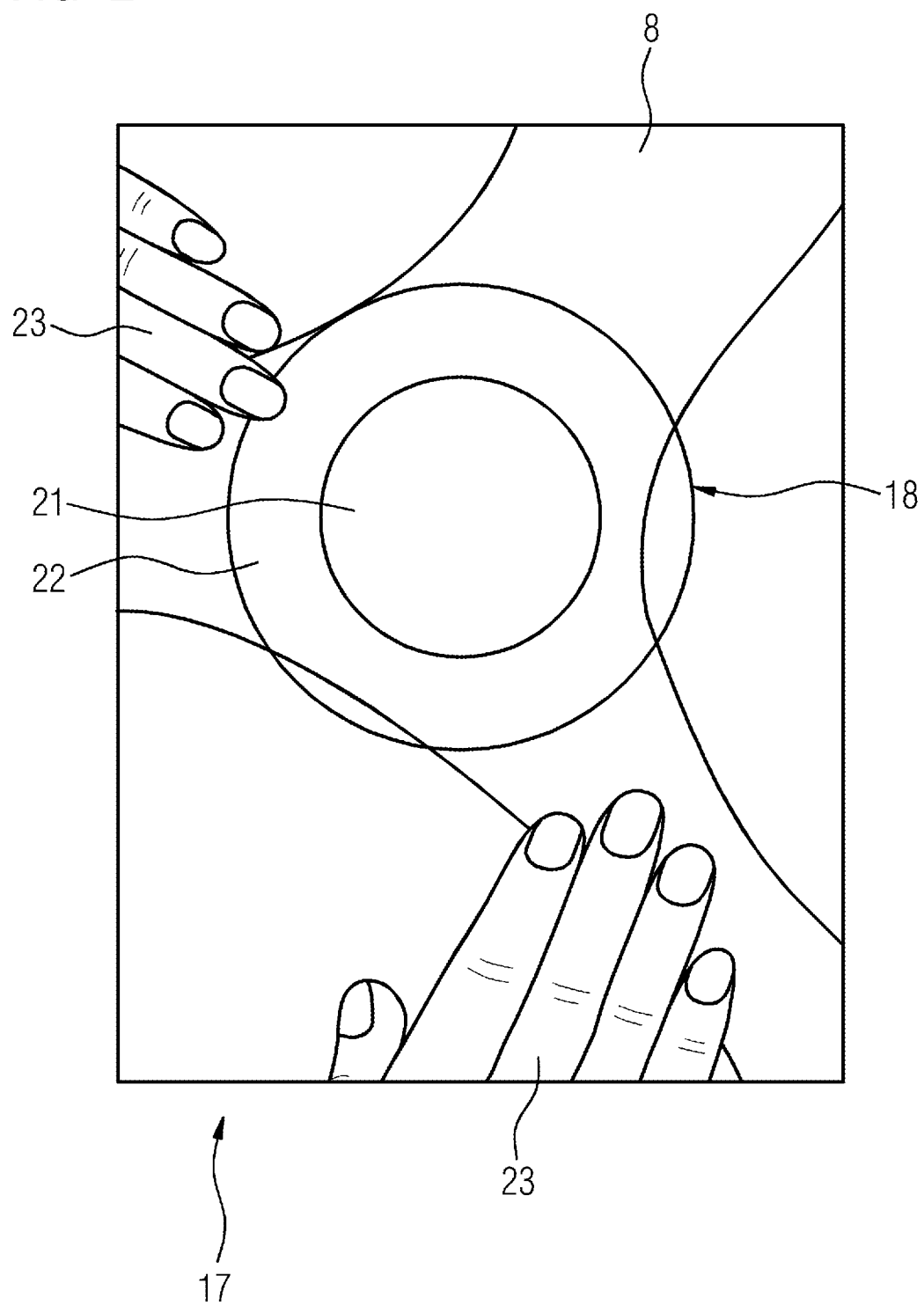
FIG. 2 is an illustration of a screen with a display according to the invention.

Following the automatic distance determination with the camera 14 or the device 26, the representation device 16 calculates the intersecting area between the patient plane 6 and the conical beam 4 and visualizes it as a virtual recording region 18, as illustrated by way of example in FIG. 2.

The apparatus 13 according to the invention for visualizing an X-ray region is configured for carrying out the described method. The representation device 16 is preferably a data processing unit, configured for carrying out all the steps according to the method described here that are related to the processing of data. This concerns in particular the ascertainment of the distance 27 by way of evaluating images of the camera 14, the calculation of the intersecting area for visualizing the virtual recording region 18, and the driving of the screen 15 for displaying the virtual recording region 18 in a suitable form in addition to the image 17 of the patient 8, in particular in multiple colors and thus so as to superpose the image 17.

The data processing unit preferably has a number of functional modules, wherein each functional module is configured for carrying out a specific function or a number of specific functions according to the described method. The functional modules can be hardware modules or software modules. In other words, the invention, to the extent that it relates to the data processing unit, can be realized either in the form of computer hardware or in the form of computer software or as a combination of hardware and software. To the extent that the invention is realized in the form of software, that is to say as a computer program, all described functions are realized by way of computer program instructions if the computer program is executed on a computer with a processor. This applies in particular to computer program instructions for calculating a virtual recording region 18 of the X-ray recording that corresponds to the intersecting area between the beam 4 and the object plane 6, and to computer program instructions for representing the virtual recording region 18 in a displayed image 17 of a region 5 of the object 8. The computer program instructions are here realized in a manner that is known per se in any desired programming language and can be made available to the computer in any desired form, for example in the form of data packets that are transmitted via a computer network, or in the form of a computer program product which is stored on a disc, a CD-ROM or another data carrier.

Even though the invention has been illustrated in detail and described by the preferred exemplary embodiment, the invention is not limited to the disclosed examples, and other variations can be derived by the person skilled in the art without departing from the scope of protection of the invention.

For example, the object plane 6 may be located at an angle relative to the X-ray receiver 3. The virtual recording region 18 in that case has—in a two-dimensional image on the screen 15 that is calculated by the representation device 16 that is embodied correspondingly by this variant—a form that differs from the circular form. The X-ray region can also be represented in three-dimensional form on the screen 15 with appropriate matching of the calculations in the representation device 16. Instead of the virtual recording region 18 in the form of an intersecting area, a (partial) volume of the beam 4 can also be represented.

The following is a summary list of reference numerals and the corresponding structure used in the above description of the invention:

1 X-ray recording system
2 X-ray source
3 X-ray receiver
4 beam
5 actual recording region
6 patient plane
7 operating table
8 patient
9 C-arm
(free)
11 central X-ray
12 detector plane
13 apparatus for visualization
14 camera
15 screen
16 representation device
17 image
18 virtual recording region
19 region located thereunder
20 (free)
21 core region
22 rim region
23 physician's hand
24 larger virtual recording region
25 object plane
26 device for ascertaining distance
27 distance 28 coordinate system of the camera
29 coordinate system of the C-arm device

The invention claimed is:

1. A method for visualizing an X-ray region formed during a production of an X-ray recording, wherein the X-ray recording relates to at least one region of an object located in an object plane, the at least one region disposed between an X-ray source and an X-ray receiver and is captured by a beam from the X-ray source, which comprises the steps of:

recording a video image of the region of the object;

displaying the video image; and representing at least a portion of the beam as an inner core region in the displayed video image and representing a rim region located outside the inner core region in the displayed video image, wherein the rim region is shown in the displayed video image in a way indicating that the rim region is exposed to lesser radiation than the inner core region.

2. The method according to claim 1, wherein a virtual recording region of the X-ray recording is represented as the portion of the beam.

3. The method according to claim 2, wherein the virtual recording region corresponds to an intersecting area between the beam and the object plane.

4. The method according to claim 2, wherein the virtual recording region is represented even before the X-ray recording is produced.

5. The method according to claim 2, wherein the virtual recording region is represented in color.

6. An apparatus for visualizing an X-ray region for use in an X-ray recording system, the X-ray recording system having an X-ray source and an X-ray receiver for producing an X-ray recording of at least one region of an object disposed in an object plane, the at least one region disposed between the source, the apparatus comprising:

a video camera for recording a video image of the region of the object;

a screen for displaying the video image;

a device for representing at least a portion of the beam as an inner core region in the displayed video image; and a data processing unit configured for causing said device to display a rim region located outside the inner core region in the displayed video image, wherein the rim region is shown in the displayed video image in a way indicating that the rim region is exposed to lesser radiation than the inner core region.

7. The apparatus according to claim 6, further comprising a device for ascertaining a distance from the object to the X-ray receiver.

8. An X-ray recording system, comprising:

an X-ray source;

an X-ray receiver for producing an X-ray recording of at least one region of an object located in an object plane, the at least one region disposed between said X-ray source and said X-ray receiver and is captured by a beam from said X-ray source;

an apparatus for visualizing an X-ray region for use in the X-ray recording system, said apparatus containing:

a video camera for recording a video image of the at least one region of the object;

a screen for displaying the video image;

a device for representing at least a portion of the beam as an inner core region in the displayed video image; and a data processing unit configured for causing said device to display a rim region located outside the inner core region in the displayed video image, wherein the rim region is shown in the displayed video image in a way indicating that the rim region is exposed to lesser radiation than the inner core region.

9. A non-transitory computer readable medium including a computer program stored thereon for visualizing an X-ray region formed during a production of an X-ray recording, wherein the X-ray recording relates to at least one region of an object disposed in an object plane, the region is disposed between an X-ray source and an X-ray receiver and being captured by a beam from the X-ray source, the computer program having computer executable instruction to be executed in a computer and programmed to:

calculate at least a portion of the beam; and represent at least one portion of the beam as an inner core region in a displayed video image of the region of the object and represent a rim region located outside the inner core region in the displayed video image, wherein the rim region is shown in the displayed video image in a way indicating that the rim region is exposed to lesser radiation than the inner core region.

* * * * *